(12) United States Patent
Gouda et al.

(10) Patent No.: US 11,957,797 B1
(45) Date of Patent: Apr. 16, 2024

(54) CHITOSAN FILM WITH TERNARY METAL OXIDES

(71) Applicant: KING FAISAL UNIVERSITY, Al-Ahsa (SA)

(72) Inventors: Mohamed Gouda, Al-Ahsa (SA); Mai Mostafa Khalaf Ali, Al-Ahsa (SA); Hany Mohamed Abd El-Lateef Ahmed, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/533,079

(22) Filed: Dec. 7, 2023

Related U.S. Application Data

(62) Division of application No. 18/224,327, filed on Jul. 20, 2023, now Pat. No. 11,883,542.

(51) Int. Cl.
| | | |
|---|---|---|
| *A61L 15/28* | (2006.01) | |
| *A61L 15/18* | (2006.01) | |
| *A61L 15/42* | (2006.01) | |
| *A61L 15/44* | (2006.01) | |
| *B82Y 5/00* | (2011.01) | |
| *B82Y 30/00* | (2011.01) | |

(52) U.S. Cl.
CPC .............. *A61L 15/28* (2013.01); *A61L 15/18* (2013.01); *A61L 15/425* (2013.01); *A61L 15/44* (2013.01); *A61L 2300/102* (2013.01); *A61L 2300/406* (2013.01); *A61L 2400/12* (2013.01); *B82Y 5/00* (2013.01); *B82Y 30/00* (2013.01)

(58) Field of Classification Search
CPC ........ A61L 15/28; A61L 15/18; A61L 15/425; A61L 15/44; A61L 2300/101; A61L 2300/406; A61L 2400/12; B82Y 5/00; B82Y 30/00
See application file for complete search history.

(56) References Cited

U.S. PATENT DOCUMENTS

| | | |
|---|---|---|
| 10,428,186 B2 | 10/2019 | Toivo et al. |
| 2010/0041292 A1 | 2/2010 | Young-Sam et al. |
| 2010/0111938 A1 | 5/2010 | Boyden et al. |
| 2011/0104052 A1 | 5/2011 | Powers et al. |
| 2013/0266628 A1 | 10/2013 | Pradeep et al. |
| 2022/0096349 A1 | 3/2022 | Kotaro et al. |

OTHER PUBLICATIONS

Alaithan et al., Improving the Durability of Chiitosan Films Through Incorporation of Tungsten, Magnesium and Graphene Oxides for Medical Applications, Chem Biodiverse, November; (20):11. (Year: 2023).*

Shariatzadeh et al. "Surface functionalization of multiwalled carbon nanotubes with chitosan and magnesium oxide nanoparticles by microwave-assisted synthesis", Polymer Composites, vol. 35, No. 10, pp. 2050-2055, 2014.

* cited by examiner

*Primary Examiner* — Carlos A Azpuru
(74) *Attorney, Agent, or Firm* — Nath, Goldberg & Meyer; Richard C. Litman

(57) ABSTRACT

A chitosan film including ternary metal oxides. In an embodiment, the ternary metal oxides can include tungsten oxide nanoparticles ($WO_3$ NPs), magnesium oxide nanoparticles (MgO NPs), and a graphene oxide (GO) layer. In an embodiment the chitosan film is porous. The chitosan film including ternary metal oxides can be used as a wound dressing for the clinical management of bacterially infected wounds.

8 Claims, 10 Drawing Sheets

US 11,957,797 B1

CHITOSAN FILM WITH TERNARY METAL OXIDES

CROSS-REFERENCE TO RELATED APPLICATION

This application is a divisional of U.S. patent application Ser. No. 18/224,327, filed on Jul. 20, 2023, the entire contents of which are incorporated herein by reference.

BACKGROUND

1. Field

The present disclosure relates to a chitosan membrane for wound healing, and in particular to a chitosan membrane with ternary metal oxides for use in wound healing.

2. Description of the Related Art

Wound healing is a complex process where the skin or another organ or tissue repairs itself after injury. Once the protective barrier is broken, an organism is susceptible to bacterial infections. Chronic bacterial infections in wounds pose a significant challenge to healthcare, hindering healing and causing complications.

Chitin and chitosan, and their derivatives, are endowed with interesting chemical and biological properties. Chitosan is a deacetylated derivative of chitin, a plentiful substance readily isolated from the shells of crustaceans such as crab, lobster, and shrimp. Antimicrobial properties of chitosan open the door to a host of medical applications, such as antimicrobial coatings for adhesive strips or wound dressings. However, products having such properties remain under development and have yet to be optimized.

Thus, a chitosan film including a ternary metal oxide solving the aforementioned problems are desired.

SUMMARY

The present subject matter relates to a chitosan (CS) composite film including ternary metal oxides. In an embodiment, the ternary metal oxides can include tungsten oxide nanoparticles ($WO_3$ NPs), magnesium oxide nanoparticles (MgO NPs), and a graphene oxide (GO) layer. In an embodiment the chitosan film is porous. The chitosan film including ternary metal oxides can be used as wound dressings for the clinical management of bacterially infected wounds.

In one embodiment, the present subject matter relates to a chitosan composite film, comprising: a polymeric matrix including chitosan; and a plurality of ternary metal oxides comprising tungsten oxide nanoparticles ($WO_3$ NPs), magnesium oxide nanoparticles (MgO NPs), and graphene oxide (GO) incorporated in or on the polymeric matrix.

In an embodiment, the chitosan composite film includes a polymeric matrix including chitosan, tungsten oxide nanoparticles ($WO_3$ NPs), magnesium oxide nanoparticles (MgO NPs), and a graphene oxide (GO) layer on the polymeric matrix. The graphene oxide thin layer can encourage charge carriers that might enhance antibacterial performance.

According to an embodiment, the present subject matter relates to a chitosan composite film includes a polymeric matrix including chitosan, tungsten oxide nanoparticles ($WO_3$ NPs) embedded within the polymeric matrix, magnesium oxide nanoparticles (MgO NPs) disposed on a surface of the polymeric matrix, and a graphene oxide (GO) layer on the polymeric matrix. The graphene oxide thin layer can encourage charge carriers that might enhance antibacterial performance.

According to an embodiment, the present subject matter relates to a chitosan composite film, includes a polymeric matrix including chitosan; and a plurality of ternary metal oxides including tungsten oxide nanoparticles ($WO_3$ NPs) having an average diameter ranging from about 80 nm to about 100 nm, magnesium oxide nanoparticles (MgO NPs) having an average diameter ranging from about 40 nm to about 50 nm, and a graphene oxide (GO) layer on the polymeric matrix.

In a further embodiment, the present subject matter relates to a wound dressing material comprising a chitosan composite film as described herein.

In one more embodiment, the present subject matter relates to a method of healing a wound in a patient comprising applying to a patient in need thereof a chitosan composite film and/or a wound dressing material as described herein at a site of the wound in the patient.

These and other features of the present subject matter will become readily apparent upon further review of the following specification.

DETAILED DESCRIPTION OF THE PREFERRED EMBODIMENTS

Figure 1:
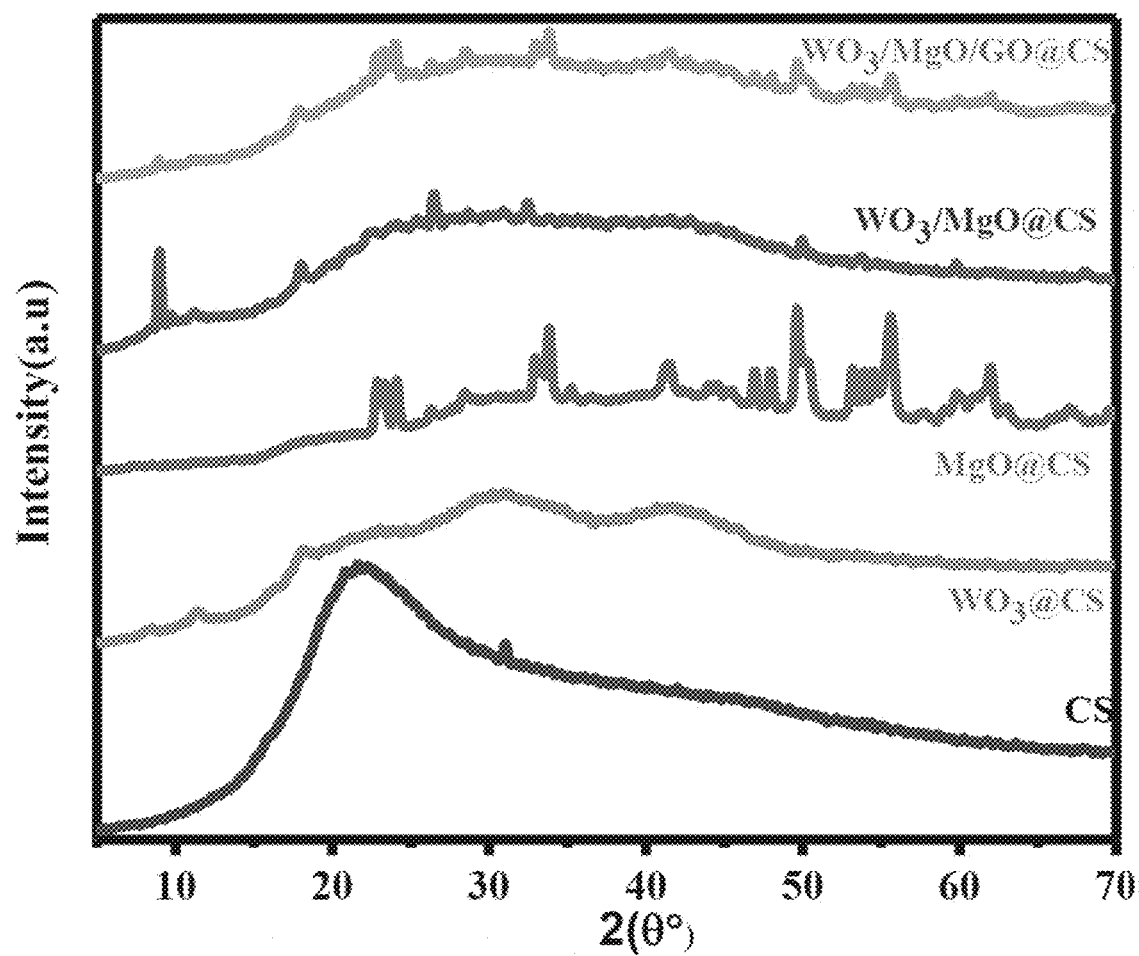
FIG. 1 shows XRD patterns of pristine chitosan and $WO_3$, MgO, $WO_3$/MgO, and $WO_3$/MgO/GO nanocomposite powder materials loaded in a CS polymer matrix (CS, $WO_3$@CS, MgO@CS, $WO_3$/MgO@CS, and $WO_3$/MgO/GO@CS, respectively).

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as an acute or chronic airway disorder or disease.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the present subject matter relates to a chitosan (CS) composite film including ternary metal oxides (also referred to herein as "$WO_3$/MgO/GO@CS"). In an embodiment, the ternary metal oxides can include tungsten oxide nanoparticles ($WO_3$ NPs), magnesium oxide nanoparticles (MgO NPs), and a graphene oxide (GO) layer. In another embodiment, the tungsten oxide nanoparticles ($WO_3$ NPs), magnesium oxide nanoparticles (MgO NPs), and graphene oxide (GO) can be in or on a polymer matrix comprising the chitosan. The chitosan film including ternary metal oxides can be used as a wound dressing for the clinical management of bacterially infected wounds.

In one embodiment, the chitosan film including ternary metal oxides may be incorporated into a wound dressing or otherwise used in medical applications. Such films may be produced by drying a stock solution including chitosan and the ternary metal oxides.

According to an embodiment, the chitosan film including ternary metal oxides is porous. As described herein, addition of $WO_3$, MgO, and GO to a chitosan film pr chitosan polymeric matrix can result in formation of a porous film with a relatively rough surface. In an embodiment, at least some of the nanoparticles can be disposed on a surface of the chitosan film, resulting in a relatively rough film surface. The chitosan film alone can have pores with dimensions ranging from about 0.8 μm to about 1.2 μm, on average. The MgO NPs can confine the flexibility of chitosan chains and make the film surface unsmooth with many minute granules and enlarged pores.

In an embodiment, the MgO NPs can be on a surface of the chitosan polymeric matrix and have a diameter ranging from about 40 nm to about 50 nm. In an embodiment, the $WO_3$ NPs can be embedded within the chitosan film. In an embodiment, the $WO_3$ NPs can have an average size ranging from about 80 nm to about 100 nm.

In an embodiment, the composite film can include a thin graphene oxide (GO) layer on a surface of the chitosan polymeric matrix. The graphene oxide layer can encourage charge carriers that might enhance antibacterial performance. In addition, incorporation of the thin GO layer can result in a composite with a more homogeneous surface and a slight increase in roughness.

According to an embodiment, the film can be hydrophilic. Accordingly, when incorporated in a wound dressing material, the film can offer a moist environment at the wound surface, which would aid in adhesion of the wound dressing material over the wounded area.

In an embodiment, the present subject matter relates to a wound dressing or a wound dressing material comprising a chitosan composite film as described herein.

In certain embodiments, the present wound dressings may comprise one or more further excipients, carriers, or vehicles. Non-limiting examples of suitable excipients, carriers, or vehicles useful herein include liquids such as water, saline, glycerol, polyethyleneglycol, hyaluronic acid, ethanol, and the like. Suitable excipients for nonliquid formulations are also known to those of skill in the art. A thorough discussion of therapeutically acceptable excipients and salts useful herein is available in Remington's Pharmaceutical Sciences, 18th Edition. Easton, Pa., Mack Publishing Company, 1990, the entire contents of which are incorporated by reference herein.

The present wound dressings typically contain a therapeutically effective dosage, e.g., a dosage sufficient to promote wound healing.

While human dosage levels have yet to be optimized for the present wound dressings, generally, a single wound dressing may contain from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many wound dressings as is required to reduce and/or alleviate the wound.

The present wound dressings have valuable therapeutic properties, which make them commercially utilizable.

According to an embodiment, the film can be prepared by adding tungsten oxide ($WO_3$) nanoparticles, magnesium oxide (MgO) nanoparticles, and graphene oxide (GO) to a solution including chitosan (CS) and stirring to provide a well-dispersed final mixture. In an embodiment, the solution including chitosan can include deionized water and acetic acid. The final mixture can then be dried to provide the film. In certain embodiments, the final mixture can be washed before it is dried.

In an embodiment, the $WO_3$ NPs and MgO NPs can be prepared by any conventional route. Similarly, the GO can be prepared using any suitable method known in the art, e.g., Hummer's method. In one embodiment, the GO can be prepared by combining graphite powder with a blend of concentrated $H_2SO_4/H_3PO_4$ under stirring to provide a mixture. Then, $KMnO_4$ can be added to the mixture with persistent stirring, followed by addition of $H_2O_2$ to provide a final solution The final solution can be washed with 30% HCl, then with distilled water, and finally with ethanol. The washed solution can then be dried in a furnace to provide graphene oxide.

In a further embodiment, the present subject matter relates to a method of healing a wound in a patient comprising applying to a patient in need thereof a chitosan composite film, a wound dressing, or a wound dressing material as described herein at a site of the wound in the patient.

In certain embodiments in this regard, the wound dressing can stimulate cell proliferation at the site of the wound in the patient.

In another embodiment, application of the wound dressing can promote metabolite circulation and vascularization.

In one embodiment of the present methods, the wound dressing can prevent a microbial, bacterial, and/or fungal infection at the site of the wound in the patient. By way of non-limiting example, the present methods can prevent infection by *E. coli* and/or *S. aureus* at the site of the wound in the patient.

In another embodiment of the present methods, the wound dressing can promote wound healing through a heightened ability to adhere to a surface of the wound.

In the above methods, the patient is preferably a mammal, more preferably a human. Furthermore, the present wound dressing can be used in combination therapy with one or more additional therapeutic agents.

The present teachings are illustrated by the following examples.

EXAMPLES

Example 1

Preparation of Chitosan Film Including Ternary Metal Oxides

First, $WO_3$ and MgO NPs were obtained. Graphene oxide was prepared by Hummer's method, as follows. A graphite powder (3 g) was added to a 9:1 blend of concentrated $H_2SO_4/H_3PO_4$ under stirring for 5 minutes. Then, 18 g of $KMnO_4$ was added to the mixture with persistent stirring for 12 h. At that point, 3 mL of $H_2O_2$ was added and mixed for 1 h. The solution was washed with 30% HCl, then with distilled water, and finally with ethanol, before it was dried in a furnace.

10 wt. % of a chitosan (CS) solution was prepared, and 5 samples of CS were prepared as stock, each comprising 20 mL of deionized water/acetic acid (9/1 v/v). The first sample was pure CS without any additives. The second sample included 0.25 g of $WO_3$ nanoparticles added to 10 mL of CS solution. The third sample included MgO nanoparticles (0.25 g) added to 10 mL of CS solution. The fourth sample included 0.125 g from $WO_3$ NPs and MgO NPs added to 10 mL of CS solution. Finally, the fifth sample included 0.1 mg, 0.1 mg, and 0.05 mg of $WO_3$ and MgO NPs, and GO, respectively, added to 10 mL of CS solution. The additives were dropped into each bottle and the solutions in each bottle were stirred using a magnetic stirrer for 1 hour to obtain well-dispersed solutions.

The solution was poured into Petri plates. An upside-down funnel was used to cover each Petri plate. Overnight, the system was left to dry naturally. The samples were collected and kept in a desiccator until their next usage after drying.

Example 2

Structural Analysis of Chitosan Film Including Ternary Metal Oxides

The solution was poured into Petri plates. An upside-down funnel was used to cover each Petri plate. Overnight, the system was left to dry naturally. The samples were collected and kept in a desiccator until their next usage after drying.

FIG. 1 shows the XRD patterns of a pure CS membrane, $WO_3$@CS, MgO@CS, $WO_3$/MgO@CS, and $WO_3$/MgO/GO@CS composite membranes, respectively. The significant peak of the CS membrane appeared at 21.9° whereas these peaks became frail in the XRD pattern of other composite membranes. The intensive diffractions for the $WO_3$@CS composite appear at 23.56°, 28.70°, 41.60, and 55.80. Accordingly, the consistent planes are (020), (111), (222), and (402), which confirm the establishment of the monoclinic phase of $WO_3$ nanoparticles that are compatible with the JCPDS card no. 89-4476. The XRD pattern of synthesized MgO@CS membrane is composed of 2θ values at 31.34°, 36.78°, 42.73°, 45.08°, and 62.17°. These peaks disclose the occurrence of a high crystalline form of MgO nanoparticles (JCPDS Card No. 75-1525).

Moreover, the XRD for the last sample of $WO_3$/MgO/GO@CS confirmed the existence of $WO_3$ and MgO in the composite in addition to a characteristic peak at 10.8° and a fragile peak at 2θ=42 related to GO nanosheets due to (002) and C (100) planes respectively. It could be seen that the peaks of MgO@CS and $WO_3$@CS have different intensities when they are both with CS in the same film. This could be due to either the high dispersion of the nanoparticles in the film or the low concentration of the nanoparticles compared to the primary films and CS concentration. These findings thus clearly demonstrate that the functionalization method was achieved efficiently through the incorporation of $WO_3$ and MgO NPs with GO nanosheets in the produced CS membranes.

Figure 2:
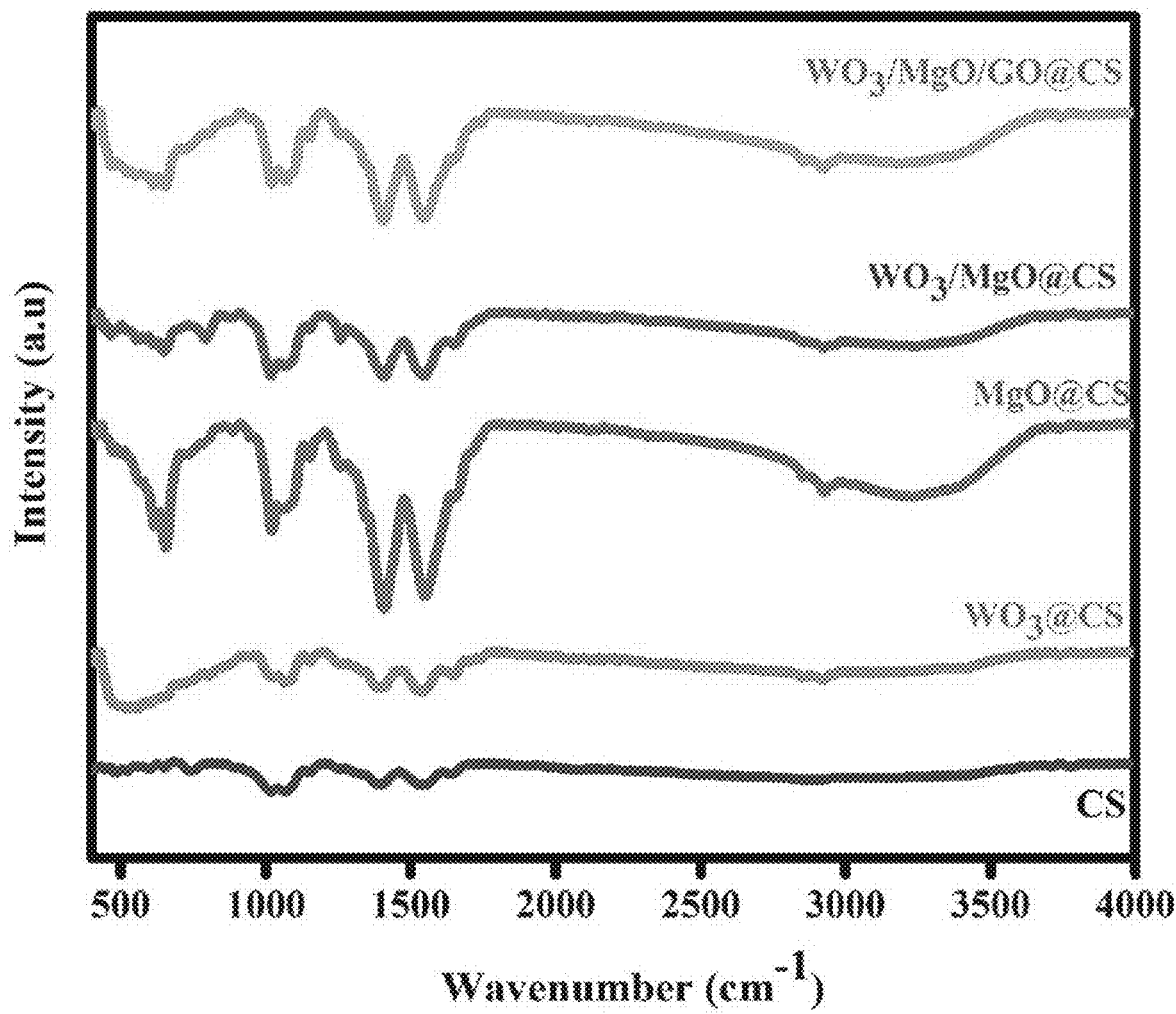
FIG. 2 shows FTIR spectra of the nanocomposites based on a CS polymer matrix including $WO_3$, MgO, $WO_3$/MgO, and $WO_3$/MgO/GO.

FT-IR spectrum of pure CS, $WO_3$/MgO@CS, and $WO_3$/MgO/GO@CS composite membranes was studied in the region 400.0-4000.0 $cm^{-1}$ (FIG. 2). Its distinctive peaks can be found at 3413, 2936, 1644, 1314, and 1016 $cm^{-1}$, which were attributed to hydroxyl and amino stretching, C—H vibrations, acetylated amino groups, C—N bond stretching, and C—O—C bond stretching, respectively, identified Chitosan. Furthermore, in the $WO_3$/MgO@CS curve, the broad absorption peaks at less than 1000 $cm^{-1}$ specify the existence of pure $WO_3$. The vibration band at 3413 $cm^{-1}$, which belongs to the hydroxyl groups of chitosan, has migrated to 3244 $cm^{-1}$ and 3283 $cm^{-1}$ by adding MgO and $WO_3$, respectively. The vibration modes of bond stretching of O—W—O are ascribed to the peaks at 824 and 791 $cm^{-1}$. Additionally, the chitosan amine groups at 1644 $cm^{-1}$ have moved to 1550 $cm^{-1}$. Previous reports have studied similar changes in the vibrational bands of the amine groups of chitosan with various metal oxides. These shifts proposed that chitosan's hydroxyl and amine groups might engage in hydrogen bonding interactions with MgO. By facilitating the effective transmission of stresses from the matrix to the filler under tensile strain, this improved interfacial contact between MgO, $WO_3$, and chitosan enhances the mechanical characteristics of the resulting membrane. Due to the very small concentration of GO in the latter composite, there is no clear characteristic peak associated with GO, most likely, the peak was confused with the amino group peak for chitosan, but its presence was previously confirmed by XRD analysis.

Figure 3A:
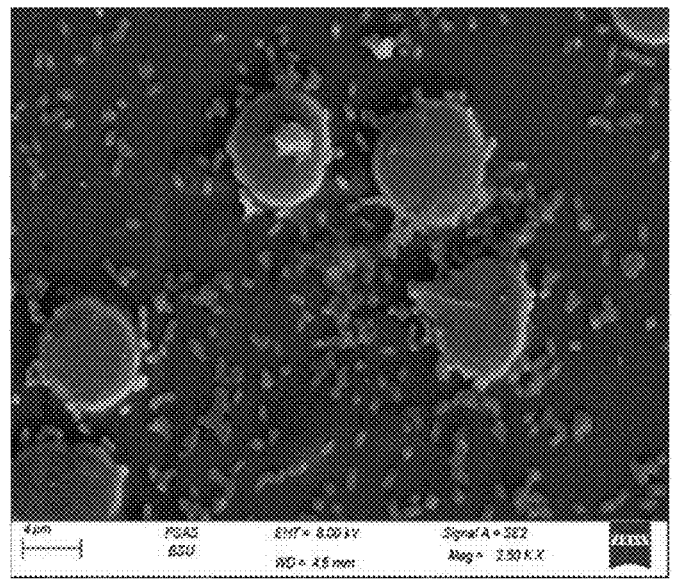
FIGS. 3A-3F show cross-sectional SEM images of (FIG. 3A) and (FIG. 3D) pure CS, (FIG. 3B) and (FIG. 3E) $WO_3$/MgO@CS, and (FIG. 3C) and (FIG. 3F) $WO_3$/MgO/GO@CS composites.
Figure 3B:
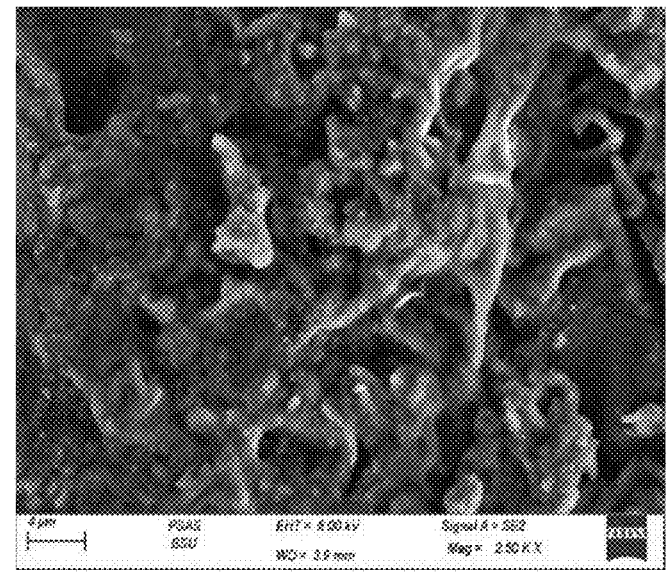
Figure 3C:
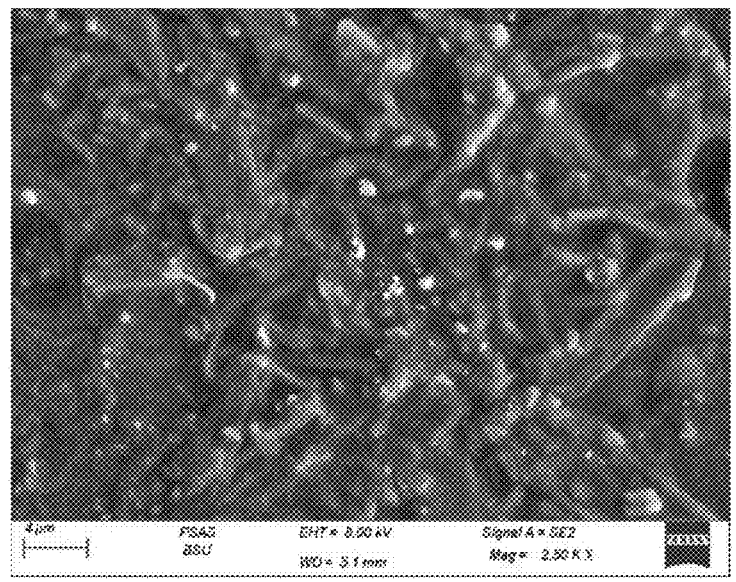
Figure 3D:
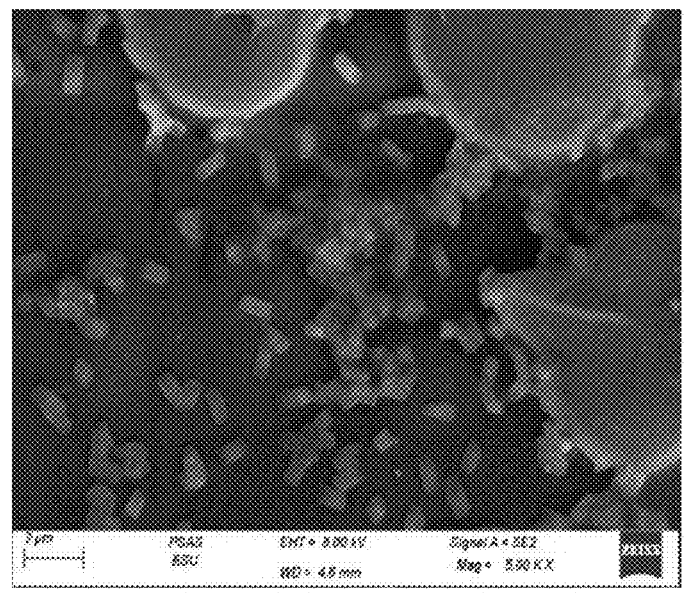
Figure 3E:
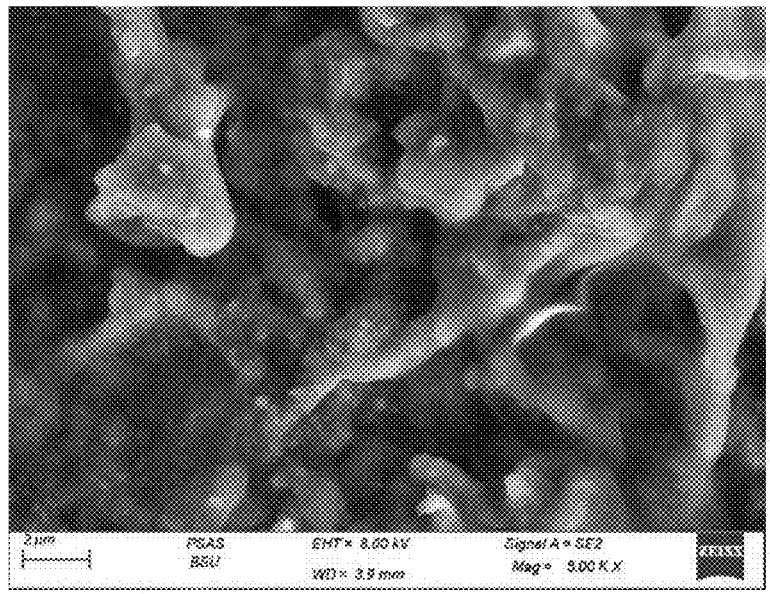
Figure 3F:
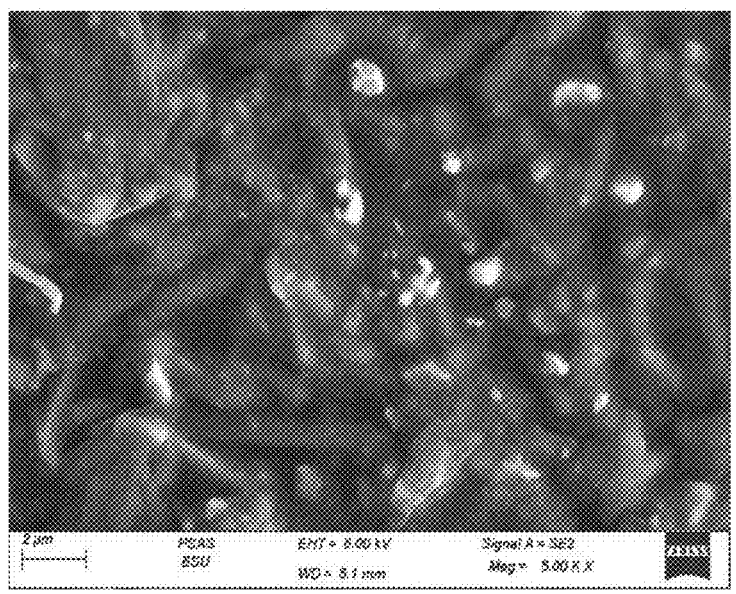

The morphology of the nanocomposite scaffold was examined by SEM investigation, and its results are presented in FIGS. 3A-3F. SEM is a technique to study the surface morphology and topography of the material. According to SEM images, surface porosity, and roughness can be studied. If the nanoparticles were embedded inside the film, the surface roughness will be very low and the film surface will be smooth. On the other hand, the surface will be rough if some of the nanoparticles were on the surface of the film. FIGS. 3A-3C show the cross-section and FIGS. 3D-3F show the higher resolution images of pure CS (FIGS. 3A and 3D), MgO@CS (FIGS. 3B and 3E), and $WO_3$/MgO/GO@CS (FIGS. 3C and 3F).

As shown in FIGS. 3A-3F, the inclusion of $WO_3$, MgO, and GO nanocomposites resulted in forming of all membranes with porous structures and a relatively rough surface. The surface morphology of pure CS only shows pores with dimensions of about (0.8 μm×1.2 μm) on average. The incorporation of MgO NPs into the membrane network confines the flexibility of chitosan chains and makes the composite membrane surface unsmooth with many minute granules and enhanced forming pores. MgO nanoparticles have diameters around 40-50 nm (FIG. 3B) and (FIG. 3E). According to FIGS. 3C and 3F, the addition of $WO_3$ NPs to nanocomposite films disclosed distinct images (white dots) on the film surface, demonstrating the $WO_3$ NPs' excellent dispersion inside the polymer matrices with an average size of 80-100 nm. As a result of the addition of GO, a new graphene oxide thin layer formed in the sample encouraged charge carriers that might enhance antibacterial performance. The surface of the composite became a more homogeneous surface with a slight increase in roughness (FIGS. 3C and 3F).

Figure 4:
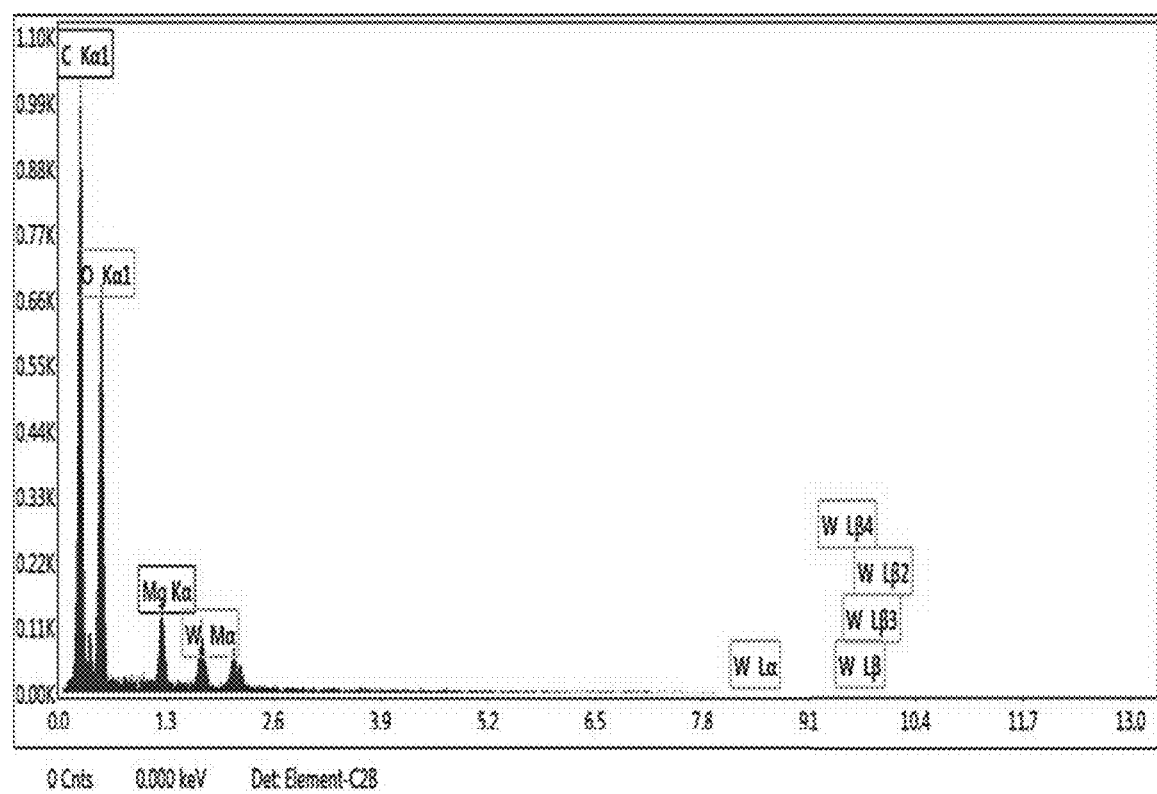
FIG. 4 shows an EDX graph of the $WO_3$/MgO/GO@S composite.

The EDX chart of the $WO_3$/MgO/GO@CS composite revealed the elemental composition of the sample (FIG. 4). As shown in FIG. 4, distinct peaks are shown for all the constituent elements, including that of the carbon, existing in GO and chitosan, the nitrogen existing in the chitosan, and both tungsten and magnesium. Correspondingly, the sharp peak of oxygen is assigned to the existence of $WO_3$ and MgO nanoparticles. The atomic percentages of all these elements are illustrated in Table 1.

TABLE 1

Elemental analysis of EDX for the composition of $WO_3$/MgO/GO@CS

| Element | Weight % | Atomic % |
| --- | --- | --- |
| C K | 47.01 | 56.89 |
| O K | 44.63 | 40.55 |
| MgK | 3.66 | 2.19 |
| WM | 4.69 | 0.37 |

Figure 5A:
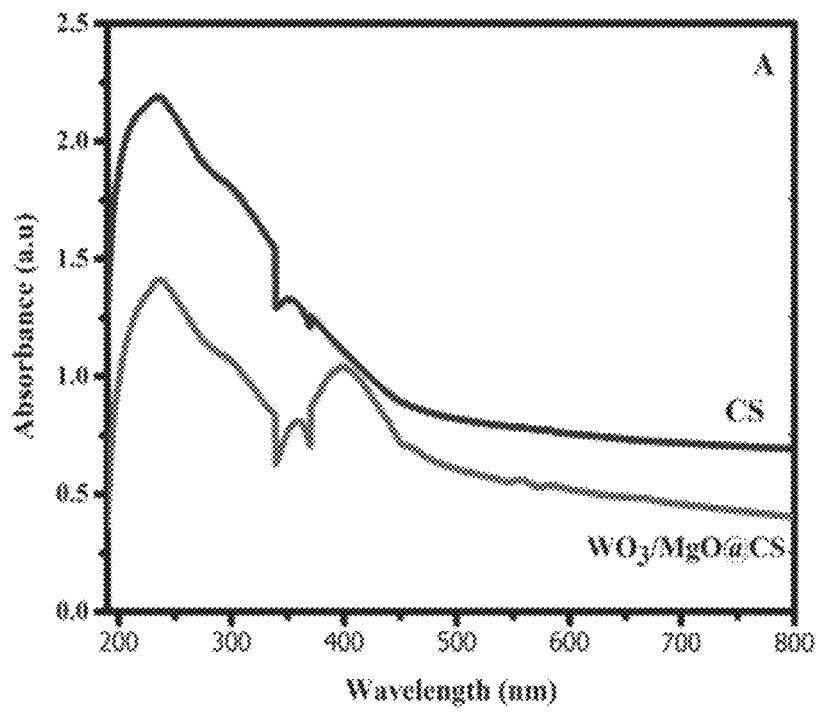
FIGS. 5(A)-5(B) show (FIG. 5A) UV-Vis spectra of the synthesized CS and WO3/MgO@CS, and (FIG. 5B) their energy band gap calculations from UV-Vis spectra data.
Figure 5B:
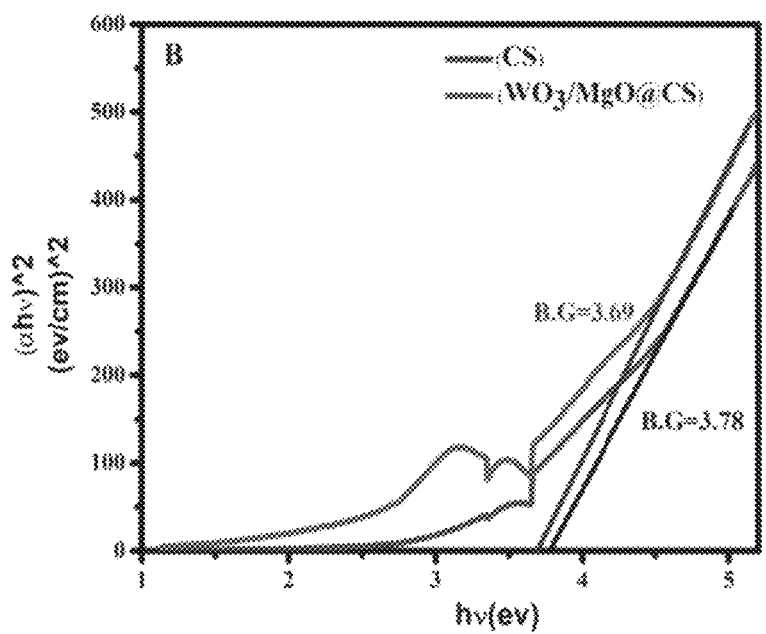

UV absorption of the chitosan nanocomposites is outlined in FIG. 5A. $WO_3$/MgO@CS composite has a much higher UV absorption than pure chitosan films. Referring to the pure CS spectra, neat chitosan films have a poor limited UV absorption peak at 238 nm compared to that of $WO_3$/MgO/GO@CS composite, which displays an absorption peak at 238 nm and a high intense absorption peak at 401 nm. These findings suggest that the UV-shielding properties of MgO nanoparticles caused the UV transmission across chitosan nanocomposite to be much lower than that through pure chitosan films. Besides, $WO_3$ NPs emphatically affected the absorption band of the $WO_3$/MgO/@CS composite and shifted towards the lower wavelength region due to its small band gap (2.9 eV). These perceptions support the effective loading of $WO_3$ on CS and their interband charge transition. To explore the impact of $WO_3$, MgO incorporation on the band-gap tuning of CS film Kubelka-Munk (KM) method was introduced. The optical absorption factor (α) can be defined as:

$$\alpha = F(R) = \frac{(1-R)^2}{2R} \quad (2)$$

where F(R) is the Kubelka-Munk function of R, and R is the reflection coefficient (R=10−A). The gap-band energy of the compounds was calculated from the plot between $(\alpha h \nu)^2$ vs. $h \nu$, as presented in FIG. 5B. By modifying $WO_3$ and MgO NPs, a significant band gap narrowing was observed to be 3.69 ev. This can be related to the insertion of metallic nanoparticles within the created CS film, which causes a transition from the valence to the conduction band with less energy due to the creation of new interstitial energy levels.

Example 3

Contact Angle

Figures 6A, 6B, 6C, 6D, 6E, 6F:
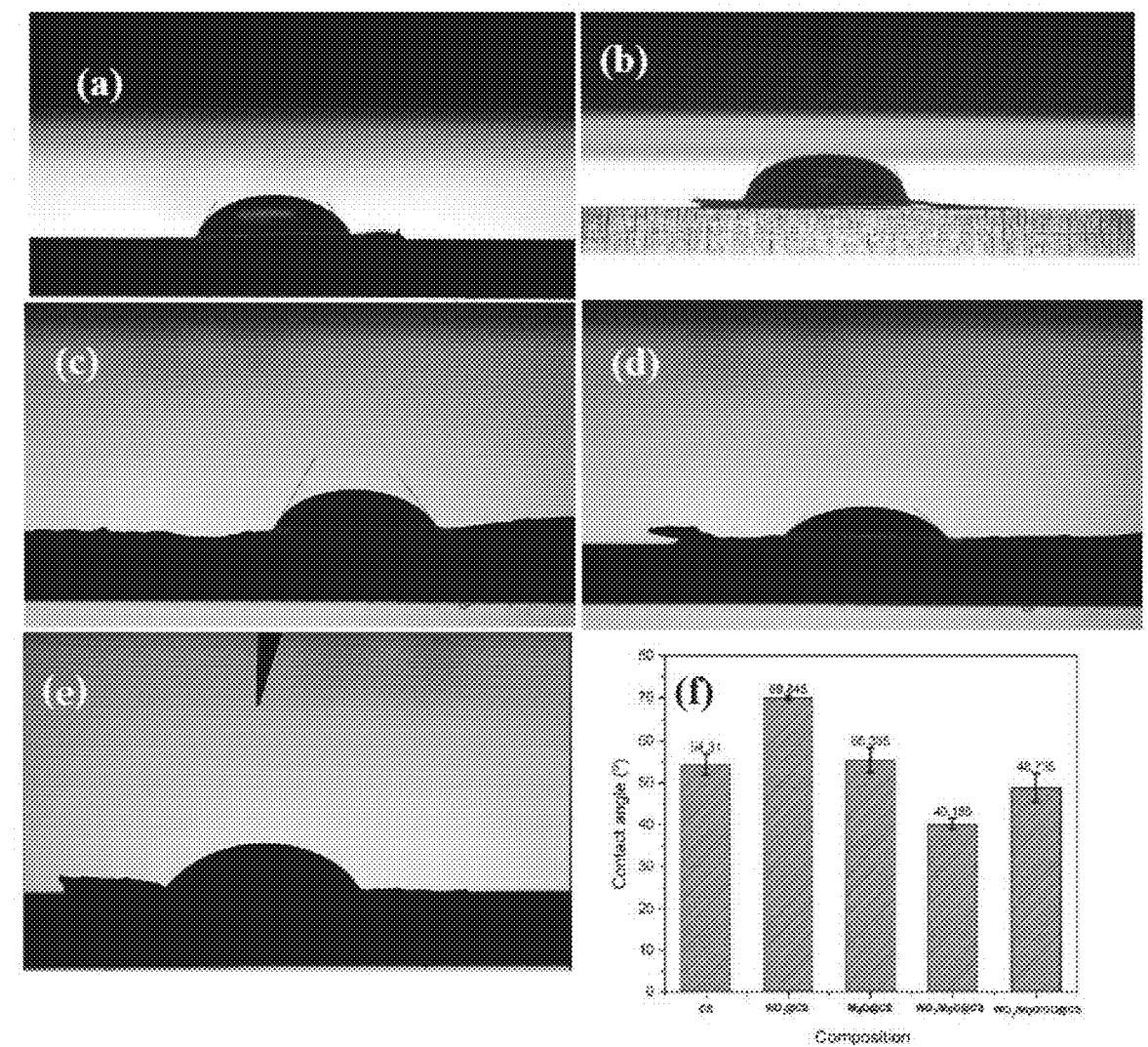
FIGS. 6A-6F are images showing dependency of contact angle on the compositional changes, with the values being 54.3°, 69.8°, 55.3°, and 40.2° for (FIG. 6A) CS, (FIG. 6B) $WO_3$@CS, (FIG. 6C) MgO@CS, (FIG. 6D) $WO_3$/MgO@CS, and (FIG. 6E) $WO_3$/MgO/GO@CS, respectively, and (FIG. 6F) a graph showing the contact angle of pure CS membrane and CS membrane loaded with $WO_3$, MgO, $WO_3$/MgO, and $WO_3$/MgO/GO.

Assessing a good dressing agent for tissue healing requires an understanding of how scaffolds interact with the surrounding environment. Furthermore, the compositional variation affects the wettability of the constructed scaffolds. The contact angle between the scaffold and the water droplets nearby indicates the scaffold's potential to be coherent with the physiological milieu. As shown in FIG. 6A, chitosan has a contact angle of about 54.31±2.46°, which indicates that its hydrophilicity is modest. The addition of $WO_3$ NPs caused a critical increment within the contact angle to be 69.84±0.51° (FIG. 6B), which decreased the hydrophilic properties of the scaffold. This can be attributed to the alteration within the surface morphology, which became more uniform and smoother with the addition of $WO_3$ NPs.

The same impact occurred by adding MgO NPs to the CS membrane, and the contact angle slightly shifted to a higher value of 55.34±2.98° (FIG. 6C). However, the incorporation of $WO_3$ and MgO NPs into the CS membrane (FIG. 6D) diminished the contact angle to almost 40.19±1.24°, which induces hydrophilicity and encourages their ability to be physically cross-linked with the surroundings, thus controlling the ratio of embedded nanoparticles through the scaffolds and playing a crucial role in adjusting its hydrophilic properties. On the other hand, the addition of GO to the previous scaffold (FIG. 6E) showed an increase in the contact angle to 48.74±3.39° which is still lower than the contact angle of pure CS. In conclusion, the created nanocomposite film may offer a moist environment at the wound surface, which would aid in the adhesion of the wound dressing material over the wounded area.

Example 4

Cell Viability

Figure 7:
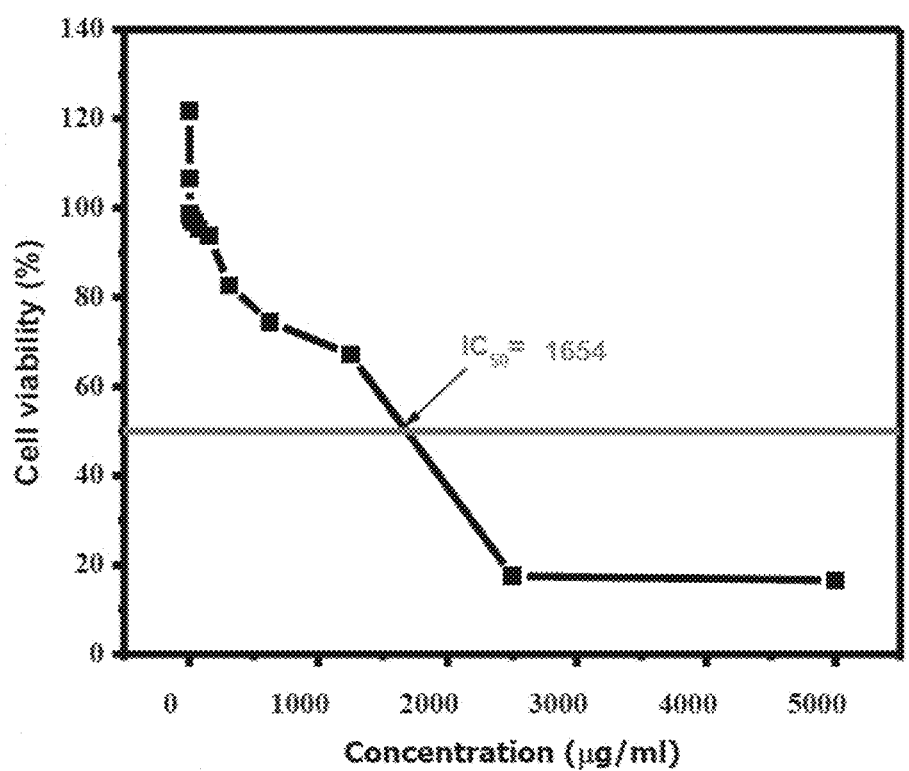
FIG. 7 is a graph showing cell viability of the $WO_3$/MgO/GO@CS composite after culturing for 3 days with normal lung cells in vitro.

The percentage of viable cells reveals how the biological system reacts to the intended biomaterial. Therefore, the cell viability of human lung cells was evaluated using an optical analyzer (FIG. 7). Cell culturing is one of the direct tests to simulate the wounded area of the injured person. It is an effective test as it gives results not only close to reality but also, sufficient to know whether the scaffold is effective in the biological medium or not. Cells are planted on the surface of the scaffold so that they can grow and multiply, since if they are planted on the lower surface of the film, they will die.

The cell viability of $WO_3$/MgO/GO@CS nanocomposites was tested after three days. The fabricated composite achieved very high values of viable cells, 121.6%. Introducing $WO_3$ and MgO NPs increases the capability of cell proliferation, with the highest $IC_{50}$ measured at 1654 µg/mL. The viable cells proliferated and grew in a concentration of 2.44 µg/mL and reached a cell viability of 121.67%. Additionally, rough surfaces and porosity caused by NPs incorporation are vital for adhesion and feeding cells with blood. This demonstrates a potential of the tested composite in cell viability. Also, addition of GO to the CS membrane improved the surface roughness, hydrophilicity, and surface area of CS scaffolds without destroying the structure of the membrane, which plays an important role in enhancing the cell proliferation ratio of the composite. This result shows the incredible biocompatibility of the fabricated composite which is recommended for tissue engineering applications. The scaffolds have been cultured for 3 days as it is real-time for the healing process. The cell viability trend showed an increase in viable cells by increasing culturing days.

Example 5

Anti-Bacterial Activity

Figure 8A:
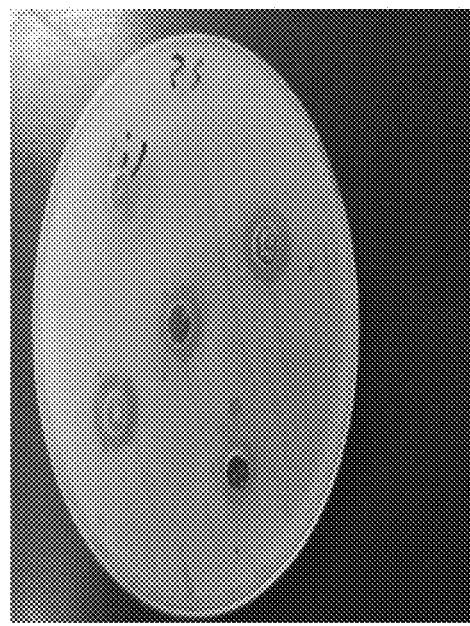
FIGS. 8A and 8B are images showing the antibacterial activity for all scaffolds against (FIG. 8A) *E. coli*, and (FIG. 8B) *S. aureus*.
Figure 8B:
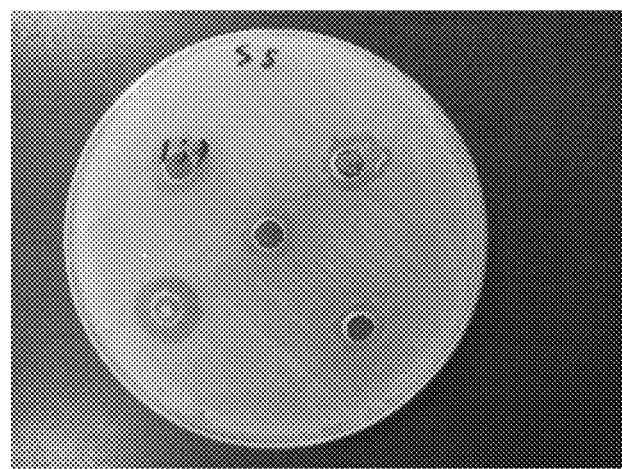

Antibacterial activity is an essential property for accelerating the wound healing process. Accordingly, it was necessary to measure the ability of scaffolds to kill bacteria. For this purpose, the antibacterial activity of the scaffold was tested against 2 types of bacteria *Escherichia coli* (*E. coli*) and *Staphylococcus aureus* (*S. aureus*). According to FIGS. 8A-8B, the pure CS film showed antibacterial activity against *E. coli* and *S. aureus* with an inhibition zone of 11.5±0.5 mm and 12.5±0.5 mm, respectively.

On the other hand, addition of MgO to CS enhanced the antibacterial activity of the scaffold against *E. coli* as the inhibition zone increased to 13±1 mm while it decreased against *S. aureus* reaching 11.5±0.5 mm. Further, the addition of $WO_3$ showed zones of inhibition equal to 8.5±0.5 mm and 10.5±0.5 mm against both *E. coli* and *S. aureus*. Additionally, the combination of both MgO and $WO_3$ in CS film demonstrated stability in the antibacterial activity of CS against *E. coli* 11.5±0.5 mm and furthermore, an increase in the antibacterial behavior against *S. aureus* with a zone of inhibition equal to 13.5±0.5 mm.

Finally, GO was added to the previous film with a very low concentration. The antibacterial activity of the scaffold against *E. coli* plateaued, while it exhibited a decrease in the behavior against *S. aureus* reaching 8.5±0.5 mm. In conclusion, it could be seen that all the scaffolds have antibacterial activity against both types of bacteria. The highest and best antibacterial activity was the scaffold of the chitosan composite film (referred to as MgO/$WO_3$@CS).

It is to be understood that the chitosan composite film is not limited to the specific embodiments described above but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A wound dressing material comprising a chitosan composite film, the chitosan composite film comprising:
   a polymeric matrix including chitosan; and
   a plurality of ternary metal oxides comprising tungsten oxide nanoparticles ($WO_3$ NPs), magnesium oxide nanoparticles (MgO NPs), and graphene oxide (GO) incorporated in or on the polymeric matrix.

2. A wound dressing material comprising a chitosan composite film, the chitosan composite film comprising:
   a polymeric matrix including chitosan; and
   a plurality of ternary metal oxides including tungsten oxide nanoparticles ($WO_3$ NPs) embedded within the polymeric matrix, magnesium oxide nanoparticles (MgO NPs) disposed on a surface of the polymeric matrix, and a graphene oxide (GO) layer on the polymeric matrix.

3. A wound dressing material comprising a chitosan composite film, the chitosan composite film comprising:
a polymeric matrix including chitosan; and
a plurality of ternary metal oxides including tungsten oxide nanoparticles ($WO_3$ NPs) having an average diameter ranging from about 80 nm to about 100 nm, magnesium oxide nanoparticles (MgO NPs) having an average diameter ranging from about 40 nm to about 50 nm, and a graphene oxide (GO) layer on the polymeric matrix.

4. The wound dressing material of claim 1, wherein the chitosan composite film is porous.

5. The wound dressing material of claim 1, wherein at least some of the MgO NPs are disposed on a surface of the polymeric matrix.

6. The wound dressing material of claim 1, wherein the $WO_3$ NPs are embedded within the polymeric matrix.

7. The wound dressing material of claim 1, wherein the MgO nanoparticles have an average diameter ranging from about 40 nm to about 50 nm.

8. The wound dressing material of claim 1, wherein the $WO_3$ NPs have an average diameter ranging from about 80 nm to about 100 nm.

* * * * *